(12) United States Patent
Suzuki

(10) Patent No.: US 8,535,698 B2
(45) Date of Patent: Sep. 17, 2013

(54) GRANULAR WATER DISPERSIBLE AGENT AND PRODUCTION PROCESS

(75) Inventor: Masahiro Suzuki, Shizuoka (JP)

(73) Assignee: Nippon Soda Co., Ltd., Tokyo (JP)

( * ) Notice: Subject to any disclaimer, the term of this patent is extended or adjusted under 35 U.S.C. 154(b) by 324 days.

(21) Appl. No.: 12/929,106

(22) Filed: Dec. 30, 2010

(65) Prior Publication Data

US 2011/0095108 A1 Apr. 28, 2011

Related U.S. Application Data

(63) Continuation of application No. 10/670,867, filed on Sep. 25, 2003, now Pat. No. 7,883,716, which is a continuation-in-part of application No. 09/913,618, filed as application No. PCT/JP00/09225 on Dec. 26, 2000, now abandoned.

(30) Foreign Application Priority Data

Dec. 28, 1999 (JP) ..................................... 11/374957
Feb. 29, 2000 (JP) .................................. 2000-57950

(51) Int. Cl.
*A01N 25/14* (2006.01)
*A01N 43/78* (2006.01)
*A01N 43/50* (2006.01)
*A01N 43/28* (2006.01)

(52) U.S. Cl.
USPC ........... 424/405; 514/365; 514/385; 514/399; 514/584; 514/587

(58) Field of Classification Search
USPC .......................................................... 424/405
See application file for complete search history.

(56) References Cited

U.S. PATENT DOCUMENTS

| | | |
|---|---|---|
| 5,001,150 A | 3/1991 | Yap |
| 5,208,030 A | 5/1993 | Hoy et al. |
| 5,980,926 A | 11/1999 | Suzuki et al. |
| 7,070,795 B1 | 7/2006 | Botts et al. |

FOREIGN PATENT DOCUMENTS

| | | |
|---|---|---|
| EP | 0 141 509 A2 | 5/1985 |
| EP | 0 853 883 A1 | 7/1998 |
| FR | 2 595 544 A1 | 9/1987 |
| JP | 40-016587 | 7/1965 |
| JP | 53-050333 A | 5/1978 |
| JP | 63-066101 A | 3/1988 |
| JP | 03-120201 A | 5/1991 |
| JP | A-03-146126 | 6/1991 |

*Primary Examiner* — Shawquia Young
(74) *Attorney, Agent, or Firm* — Foley & Lardner LLP

(57) ABSTRACT

A water dispersible granule formulation prepared by pulverized a part of active ingredients into fine particles under wet milling and pulverized another part of the active ingredients into coarse particles under dry milling, then kneading the both active ingredients for the granulation, and a process for producing the water dispersible granule formulation are disclosed. The water dispersible granule formulation according to the present invention is applicable from production of a water dispersible granule formulation comprising an active ingredient which is easily decomposed owing to environmental conditions and allows to provide the water dispersible granule formulation provided with enhanced initial and residual biological activities.

5 Claims, No Drawings

GRANULAR WATER DISPERSIBLE AGENT AND PRODUCTION PROCESS

This is a continuation of application Ser. No. 10/670,867, filed Sep. 25, 2003, which is a continuation-in-part of application Ser. No. 09/913,618, filed Aug. 13, 2001, now abandoned, which is a national stage application of PCT/JP00/09225, filed Dec. 26, 2000. The entire disclosures of the prior applications are hereby incorporated by reference herein in their entirety.

FIELD OF INVENTION

The present invention is related to a water dispersible granule formulation for an agricultural chemical and a process for producing said water dispersible granule formulation.

BACKGROUND ART

Until today, active components to be used as an agricultural chemical having insecticidal, fungicidal or herbicidal activity have been formulated into a wettable powder, an emulsifiable concentrate, a suspension concentrate, dust, etc. and have been used in such a formulation form depending upon the physical and chemical property and the application purpose. However, among the formulation types described above, an emulsifiable concentrate has a problem of environmental pollution caused by organic solvents contained therein, and a suspension concentrate has a problem of easily causing separation of the components into phases during the preservation for a long time since the active ingredient(s) is dispersed in an aqueous solvent used for the formulation. Further, a wettable powder formulation and a powder formulation has a problem in safety for human bodies as they easily cause the dusting at the production process and at the places to practically use them. Due to such problems, several water dispersible granule formulations have been provided recently in order to settle such problems.

Normally, the water dispersible granule formulation is prepared according to so-called extrusion method, which is combining a solid active ingredient, a carrier comprising minerals in fine powder, surface active agents, etc., pulverizing the combined mixture by using a dry mill, then adding bound water to the mixture and kneading the mixture by using a kneader, and forcibly extruding the kneaded mixture to pass it through a multiporous plate containing a plurality of pores with the diameter of 0.5-2.0 mm.

However, if the active ingredient has a low melting point, or if the active ingredient has a peculiar property of being hardly pulverized into fine particles, dry milling method has not been applicable for such use.

In addition, in case of dry milling method, the particle size of the pulverized components in a formulation is normally in a range of from 5 to 20 μm, thus it is difficult to pulverize the components into a size ranging from 3 to 5 μm or less so that there is a problem that the dry milling method cannot be used for the production of the water dispersible granule, particularly when the active ingredient has a low melting point, or the active ingredient is required to be pulverized into fine particles ranging from 3 to 5 μm or less in order to enhance the biological activity.

Generally, contacting area of an active ingredient with a growing plant gets small when the particle size of the active ingredient is coarse, and the total amount of the active ingredient attached onto vegetable leaves is reduced. For example of an insecticide, the initial insecticidal activity, namely the activity just after the application of the insecticide, may be deteriorated because the penetrating amount of the active ingredient into leaves and the contact frequency between a pest insect and the active ingredient particles on leaves may be generally reduced.

As a formulation process for resolving the problems as described above, a process to formulate a water dispersible granule is known, where an active ingredient for an agricultural chemical is pulverized into fine particles under wet milling, kneading the ground active ingredient with a carrier consisting of minerals, and granulating the obtained mixture by extrusion. (See, for example, JP laid-open 3-146126 gazette).

However, when an active ingredient which may be easily decomposed owing to environmental conditions is used for production of a water dispersible granule by kneading the active ingredient with a carrier consisting of minerals following to the wet milling of the active ingredient and then granulating the kneaded product, the residual activity of the active ingredient tends to be remarkably deteriorated due to decomposing effect given by light, water and the like since the particle size of the pulverized active ingredient into fine particles is generally so small as much as 1-5 μm.

Furthermore, constraint of water supply at the wet milling is imposed due to the required amount abound water at the kneading, thereby further constraining the amount of the active ingredient to be subjected to the wet milling, which has made hard to produce a water dispersible granule containing high content of the active ingredient.

Therefore, if the active ingredient is required to be pulverized into fine particles to enhance the biological activity and is the one that is easily decomposed owing to environmental conditions, it is difficult to obtain a water dispersible granule formulation provided with high initial and residual activities according to a conventional process for preparing water dispersible granule formulations.

Besides, in such cases that (1) a water dispersible granule contains different active ingredients and one of which cannot be pulverized into fine particles by dry milling method, and (2) a water dispersible granule contains different active ingredients, one of which is required to be pulverized into fine particles by wet milling in order to enhance the initial activity, and the other may be pulverized by either wet or dry milling but is required to be pulverized roughly in order to raise the content of the active ingredients in the formulation or enhance the residual activity, it was so hard to employ a process of kneading and granulating materials following to dry milling and a process of kneading and granulating materials following to wet milling for the production of a water dispersible granule formulation.

DISCLOSURE OF THE INVENTION

It is an object of the present invention to provide a water dispersible granule formulation, which can enhance the initial and residual activity of an active ingredient contained in the formulation.

The present invention firstly provides a water dispersible granule formulation containing the same or different active ingredient(s) workable as an agricultural chemical and having different average particle sizes (particle diameter distribution) from one to another.

The water dispersible granule formulation according to the present invention is preferably prepared by mixing and granulating the first active ingredient pulverized into fine particles by wet milling and the second active ingredient pulverized by dry milling.

Further, the average particle size of the first active ingredient is preferably in a range of from 0.5 to 5 μm, and the average particle size of the second active ingredient is preferably in a range of from 3 to 30 μm.

In the water dispersible granule formulation according to the present invention, the first active ingredient is preferably in solid form and hardly soluble in water and the solubility in water is preferably less than 1,000 ppm.

As designative examples for the first active ingredient, one or more compounds selected from a group consisting of triflumizole, thiuram, fluazinam, anilazine, captan, hexythiazox, benzoximate, tebufenpyrad, ziram, thiophanate methyl, mepanipyrim and N'-cyclopropylmethyloxy-N-phenylacetyl-2,3-difluoro-6-trifluoromethylbenzamidine may be given.

As the second active ingredient to be pulverized by dry milling, any compound being in solid state at an ambient temperature and has a melting point higher than 30° C. may be used without limitation, and two or more of such compounds may be used as the second active ingredient.

The present invention secondary provides a process to produce a water dispersible granule formulation comprising steps of combining the first active ingredient, a wetting and dispersing agent and water each in a given amount and then grinding the combined mixture under wet milling, combining the second active ingredient, a fine carrier consisting of minerals and a wetting and dispersing agent each in a given amount and then pulverizing under dry milling, and mixing the mixture obtained in the wet milling process and the mixture obtained in the dry milling and then granulating the obtained mixture.

In the second invention described above, the process to grind under wet milling preferably contains a process to prepare the average particle size of the active ingredient to a range of from 0.5 to 5 μm, and the process to pulverize under dry milling preferably contains a process to prepare the average particle size of the active ingredient to a range of from 3 to 30 μm.

According to the process of the present invention, the following types of water dispersible granule formulations may be provided.

(1) The water dispersible granule formulation comprising the first active ingredient which is required to be pulverized into fine particles for enhancement of the initial biological activity or cannot be pulverized into fine particles by the dry milling due to the own peculiar property and the second active ingredient which is required to be pulverized into coarse particles for enhancement of the residual activity or to increase the content in the formulation, wherein the first and the second active ingredients may be the same or different with each other.

(2) The water dispersible granule formulation, wherein the first and the second active ingredients are the same, which is provided with highly-effective initial biological activity and highly-effective residual activity by means of pulverizing the part of the active ingredient into fine particles by means of the wet milling and of pulverizing the remainder into coarse particles by means of the dry milling.

(3) The water dispersible granule formulation, wherein the first and the second active ingredients are different with each other, the first active ingredient that cannot be pulverized by the dry milling due to the own peculiar property is pulverized into fine particles by means of the wet milling, and the second active ingredient that is required to be pulverized into coarse particles for enhancement of the residual activity or to increase the content is pulverized by means of the dry milling.

PREFERRED EMBODIMENTS FOR THE INVENTION

Now, the present invention is explained in detail in the following.

The present invention is (1) to provide a water dispersible granule formulation provided with highly-effective initial and residual activities comprising the first and the second active ingredients both workable as an agricultural chemical and are the same compound, which is provided with highly-effective initial biological activity and residual activity by preparing the particle size of both active ingredients different with each other by means of wet milling and dry milling, and (2) to provide a water dispersible granule formulation comprising the first and the second active ingredient both workable as an agricultural chemical and are different compounds with each other, wherein the first active ingredient is required to be pulverized into fine particles by means of wet milling in order to enhance its initial biological activity or if it cannot be pulverized by means of dry milling due to the own peculiar property, and the second active ingredient can be pulverized into coarse particles by either wet milling or dry milling but is required to be pulverized in order to enhance its residual activity or to increase its content in the formulation.

The first active ingredient contained in the water dispersible granule formulation according to the present invention is preferably in solid state at an ambient temperature and hardly soluble in water, and more preferably, the active ingredient has solubility in water of 1,000 ppm or less.

As designative examples for the first active ingredient describe above, one or more compounds selected from a group consisting of triflumizole, thiuram, fluazinam, anilazine, captan, hexythiazox, benzoximate, tebufenpyrad, ziram, thiophanate methyl, mepanipyrim and N'-cyclopropylmethyloxy-N-phenylacetyl-2,3-difluoro-6-trifluoromethylbenzamidine may be given.

As the second active ingredient to be contained in the water dispersible granule formulation according to the present invention, any compound being in solid state at an ambient temperature and has a melting point higher than 30° C. may be used without limitation, and two or more of such compounds may be combined, and the similar ones as exampled above for the first active ingredient may be used as the second active ingredient as well.

The first feature of the present invention is directed to the difference in the average particle sizes of the plural active ingredients, or particle size distribution in other word, respectively obtainable by wet milling and dry milling. Consequently, a compound as the first active ingredient and a compound as the second active ingredient to be used may be the same or different with each other.

In the present invention, as examples for the wetting and dispersing agent to be combined at the wet milling, polyoxyethylene, polyoxypropylene, copolymer of polyoxyethylene and polyoxypropylene, sodium alkylbenzenesulfonate, alkylphosphoric ester added with polyoxyethylne, aliphatic amines added with polyoxyethylene, aliphatic alcohols added with polyoxyethylene, tween-type surface active agent of sorbitanmonooleate, sorbitantrioleate and the like added with polyoxyethylene, span-type surface active agent of sorbitanmonooleate, sorbitantrioleate and the like, castor oil ester added with polyoxyethylene, tristyrylphenyl ether or distyrylphenyl ether added with polyoxyethylene, tristyrylphenyl ether phosphate added with polyoxyethylene, distyrylphenyl ether sulfate added with polyoxyethylene, alcohol ether added with polyoxyethylene, sodium alkylnaphthalenesulfonate, sodium laurylsulfate, sodium ligninsulfonate, formaldehyde condensate of sodium alkylnaphthalenesulfonate, formaldehyde condensate of sodium phenolsulfonate, copolymer of isobutylene and maleic anhydride, and sodium polycarboxylate may be given, and two or more of the exampled compounds described above may be used in a combination as the wetting and dispersing agent.

As examples for the wetting and dispersing agent to be combined at the dry milling, sodium alkylnaphthalenesulfonate, sodium alkylbenzenesulfonate, sodium laurylsulfate, sodium ligninsulfonate, formaldehyde condensate of sodium alkylnaphthalenesulfonate, aldehyde condensate of sodium phenolsulfonate, copolymer of isobutylate and maleic anhydride, sodium polycarboxylate, sodium dioctylsulfosuccinate, higher alcohol sulfuric ester sodium and the like may be given, and two or more of the compounds exampled above may be used in combination as the wetting and dispersing agent.

As examples for the fine carrier consisting of minerals to be combined at the dry milling process, an inorganic salt, such as potassium chloride, calcium carbonate, ammonium sulfate, potassium phosphate and sodium phosphate, diatomaceous earth, bentonite, pyrophilite-type clay and caolinite-type clay may be given, and two or more of the compounds exampled above may be used in combination as the carrier.

In addition, silicon series surfactants, sodium and calcium salts of a higher fatty acid, the mixture thereof, acetylene-type surfactants, and the like may be added to the water dispersible granule formulation to reduce foaming at the wet milling and at the dilution process.

The contents of each components in the water dispersible granule formulation according to the present invention differ depending on the type of the active ingredient, however, as a ratio relative to the total formulation, the content of the active ingredient in total is in a range of 0.02-90 wt %, and preferably in a range of 0.02-70 wt %, and the amounts of the active ingredient to be contained at the wet milling process and at the dry milling may be arbitrary varied. The amount of the wetting and dispersing agent to be added at the wet milling is in a range of 1-10 wt %, and preferably in a range of 1-5 wt %, and the amount of the wetting and dispersing agent to be added at the dry milling is in a range of 1-30 wt %, and preferably in a range of 5-20 wt %. The amount of the carrier comprising fine powder minerals is in a range of 1-50 wt %, and preferably in a range of 10-40 wt %, and the amount of the anti-foaming agent is less than 5 wt % and is preferably less than 3 wt %.

The water dispersible granule formulation, hereinafter might be abbreviated as WDG, of the present invention is produced as explained below.
(1) An active ingredient, a wetting and dispersing agent and an anti-foaming agent are dissolved in water, dispersed and then pulverized into fine particles under wet milling to prepare a suspension to be used for the water dispersible granule formulation, said suspension hereinafter might be abbreviated as WDG-SC.
(2) An active ingredient, a wetting and dispersing agent and a carrier comprising fine powder minerals are mixed and pulverized under dry milling process to prepare wettable powder to be used for the water dispersible granule formulation, said wettable powder might be abbreviated as WDG-WP.
(3) The obtained WDG-SC is added to the WDG-WP, and the resulting mixture is added with bound water, kneaded by using a kneader, and passed through multiporous plate containing pores each of which diameter is ranging from 0.5 to 2.0 mm to obtain granulated moist mixture in noodle-like shape, and the granulated mixture is dried by using an appropriate dryer to obtain the objective water dispersible granule formulation.

As a granulation method, any method may be employed if it has been used in producing granular formulation for an active ingredient for plant protection use. As examples for the granulation method, extrusion, agitation, breaking, fluid bed, spray dryer, etc. may be given. The particle size and the appearance of the granular formulation may be arbitrary modified depending upon the objective use, such as the type of an active ingredient and the dilution process.

EXAMPLES

Now, the present invention is further described in detail with referring the examples in the following, however, it should be noted that the scope of the present invention is not limited to the description in the examples, and the first and the second active ingredients, various types of additives, and the combination ratio may be modified without limitation as far as the modification does not exceed the scope of the subject matter of the present invention.

Example 1

N'-cyclopropylmethyloxy-N-phenylacetyl-2,3-difluoro-6-trifluoromethylbenzamidine, (hereinafter designated as "compound A"), in an amount of 100 g, tristyrylphenyl ether added with polyoxyethylene of which HLB being 15 more or less in an amount of 10 g, sodium polycarboxylate in an amount of 10 g and a silicon series anti-foaming agent in an amount of 2.5 g were mixed and added with distilled water in an amount of 150 g, and the resulting mixture was dissolved and dispersed by using polytron. The dispersed mixture was then pulverized into fine particles under wet milling wherein zircon beads with a diameter of 1 mm are used by using Eiger motor mill (manufactured by EIGER JAPAN Co. Ltd.) to prepare the WDG-SC of the compound A having the average particle size of 1.5 μm.

Then, triflumizole in an amount of 100 g, sodium alkylnaphthalenesulfonate in an amount of 10 g, formaldehyde condensate of sodium alkylnaphthalenesulfonate in an amount of 140 g, sodium ligninsulfonate in an amount of 80 g, diatomaceous earth in an amount of 300 g and potassium chloride in an amount of 237.5 g were mixed and then pulverized into coarse particles under dry milling to prepare the WDG-WP containing triflumizole, wherein the average particle size of particles containing triflumizole is 7 μm.

To the obtained WDG-WP in am amount of 877.5 g, the WDG-SC (272.5 g) obtained above and distilled water (180 g) were added, and the resulting mixture was then kneaded by using Bench Kneader (manufactured by Irie Shokai Co. Ltd.), granulated into moist granular product in noodle-like shape with a diameter of 0.6 mm by using micro-type granule preparation apparatus (manufactured by Tsutsui Rikagaku Kikai Co., Ltd.) and dried at 40□ for 12 hours by using a blowing drier to prepare the WDG (WDG-1) of the Example 1.

Example 2

The compound A in an amount of 100 g, distyrylphenyl ether added with polyoxyethylene of which HLB being 15 more or less in an amount of 10 g, sodium polycarboxylate in an amount of 10 g and silicon series anti-foaming agent in an amount of 2.5 g were mixed and added with distilled water in an amount of 150 g, and the resulting mixture was pulverized into fine particles under wet milling according to the same procedure as described in the Example 1 to prepare the WDG-SC of the compound A having the average particle size of 3.0 µm.

Then, triflumizole in an amount of 300 g, sodium alkylnaphthalenesulfonate in an amount of 10 g, sodium alkylbenzenesulfonate in an amount of 10 g, formaldehyde condensate of sodium alkylnaphthalenesulfonate in an amount of 140 g, sodium ligninsulfonate in an amount of 80 g, diatomaceous earth in an amount of 200 g and potassium chloride in an amount of 137.5 g were mixed and then pulverized into coarse particles according to the same process as described in the Example 1 to prepare the WDG-WP containing triflumizole, wherein the average particle size of particles containing triflumizole is 6 µm.

Then, the obtained WDG-WP in an amount of 877.5 g was added with the WDG-SC in an amount of 272.5 g and distilled water in an amount of 150 g, and the resulting mixture was processed according to the procedure as described in the Example 1 to prepare the WDG (WDG-2) of the Example 2.

Example 3

The compound A in an amount of 150 g, tristyrylphenyl ether added with polyoxyethylene of which HLB being 15 more or less in an amount of 10 g, sodium polycarboxylate in an amount of 10 g and silicon series anti-foaming agent in an amount of 2.5 g were mixed and then added with distilled water in an amount of 125 g, and the resulting mixture was pulverized into fine particles under wet milling according to the same procedure as described in the Example 1 to prepare the WDG-SC containing the compound A having the average particle size of 1.5 µm.

Then, thiophanate methyl in an amount of 600 g, sodium alkylnaphthalenesulfonate in an amount of 10 g, formaldehyde condensate of sodium alkylnaphthalenesulfonate in an amount of 50 g, sodium ligninsulfonate in an amount of 25 g, calcium carbonate in an amount of 100 g and potassium chloride in an amount of 42.5 g were mixed and then pulverized into coarse particles under dry milling according to the same procedure as described in the Example 1 to prepare the WDG-WP containing thiophanate methyl of which particles having the average particle size of 7 µm.

To the obtained WDG-WP in an amount of 827.5 g, the WDG-SC in an amount of 297.5 g and distilled water in an amount of 75 g were added to obtain the WDG (WDG-3) of the Example 3 according to the same procedure as described in the Example 1.

Example 4

Triflumizole in an amount of 100 g, block copolymer of polyoxyethylene of which HLB being 14 more or less and polyoxypropylene in an amount of 50 g, formaldehyde condensate of sodium phenolsulfonate in an amount of 70 g and silicon series anti-foaming agent in an amount of 2.5 g were mixed and then added with distilled water in an amount of 200 g, and the resulting mixture was pulverized into fine particles under wet milling according to the same procedure as described in the Example 1 to prepare the WDG-SC containing triflumizole of which average particle size being 5.0 µm.

Then, thiophanate methyl in an amount of 600 g, sodium alkylnaphthalenesulfonate in an amount of 10 g, formaldehyde condensate of sodium alkylnaphthalenesulfonate in an amount of 25 g, sodium ligninsulfonate in an amount of 25 g, calcium carbonate in an amount of 100 g and potassium chloride in an amount of 17.5 g were mixed and then pulverized into coarse particles under dry milling according to the same procedure as described in the Example 1 to prepare the WDG-WP containing thiophanate methyl of which particles having the average particle size of 7 µm.

To the obtained WDG-WP in an amount of 777.5 g, the WDG-SC in an amount of 422.5 g and distilled water in an amount of 30 g were added to obtain the WDG (WDG-4) of the Example 4 according to the same procedure as described in the Example 1.

Example 5

Triflumizole in an amount of 100 g, tristyrylphenyl ether added with polyoxyethylene of which HLB being 15 more or less in an amount of 10 g, sodium polycarboxylate in an amount of 10 g and silicon series anti-foaming agent in an amount of 2.5 g were mixed and then added with distilled water in an amount of 150 g, and the resulting mixture was pulverized into fine particles under wet milling according to the same procedure as described in the Example 1 to prepare the WDG-SC containing triflumizole of which average particle size being 2 µm.

Then, triflumizole in an amount of 200 g, sodium alkylnaphthalenesulfonate in an amount of 20 g, sodium alkylbenzenesulfonate in an amount of 10 g, formaldehyde condensate of sodium alkylnaphthalenesulfonate in an amount of 140 g, sodium ligninsulfonate in an amount of 80 g, diatomaceous earth in an amount of 300 g and potassium chloride in an amount of 127.5 g were mixed and then pulverized into coarse particles under dry milling according to the same procedure as described in the Example 1 to prepare the WDG-WP of which particles containing triflumizole having the average particle size of 8 µm.

To the obtained WDG-WP in an amount of 877.5 g, the WDG-SC obtained above in an amount of 272.5 g and distilled water in an amount of 180 g were added, and the resulting mixture was kneaded by using Bentch Kneader (manufactured by Irie Shokai Co., Ltd.) and granulated into the moist noodle-shaped product having the diameter of 0.6 mm by using a micro-type granules preparation apparatus (manufactured by Tsutsui Rikagaku Kikai Co., Ltd.) and dried at 40□ for 12 hours by using a blowing dryer to obtain the WDG (WDG-5) of the Example 5.

Example 6

Thiophanate methyl in an amount of 100 g, tristyrylphenyl ether added with polyoxyethylene of which HLB being 15 more or less in an amount of 10 g, sodium polycarboxylate in an amount of 10 g and silicon series anti-foaming agent in an amount of 2.5 g were mixed and then added with distilled water in an amount of 150 g, and the resulting mixture was pulverized into fine particles under wet milling according to the same procedure as described in the Example 1 to prepare the WDG-SC containing triflumizole of which average particle size being 2 µm.

Then, thiophanate methyl in an amount of 600 g, sodium alkylnaphthalenesulfonate in an amount of 10 g, formaldehyde condensate of sodium alkylnaphthalenesulfonate in an amount of 50 g, sodium ligninsulfonate in an amount of 25 g, calcium carbonate in an amount of 100 g and potassium chloride in an amount of 92.5 g were mixed and then pulverized into coarse particles under dry milling according to the same procedure as described in the Example 1 to prepare the WDG-WP of which particles containing thiophanate methyl having the average particle size of 7 µm.

To the obtained WDG-WP in an amount of 877.5 g, the WDG-SC obtained above in an amount of 272.5 g and distilled water in an amount of 150 g were added to obtain the WDG (WDG-6) of the Example 6 according to the same procedure as described in the Example 1.

The compositions of the formulations obtained in the examples described above are shown in Table 1.

TABLE 1

| Example | 1 | 2 | 3 | 4 | 5 | 6 |
|---|---|---|---|---|---|---|
| WDG-SC | | | | | | |
| Compound A | 100 | 100 | 150 | | | |
| Triflumizole | | | | 100 | 100 | |
| Thiophanate methyl | | | | | | 100 |
| POE tristyrylphenyl ether | 10 | | 10 | | 10 | 10 |
| POE distyrylphenyl ether | | 10 | | | | |
| POE-POP block copolymer | | | | 50 | | |
| Formaldehyde condensate of Sodium phenolsulfonate | | | | 70 | | |
| Sodium polycarboxylate | 10 | 10 | 10 | | 10 | 10 |
| Silicon-containing defoaming agent | 2.5 | 2.5 | 2.5 | 2.5 | 2.5 | 2.5 |
| Distilled water | 150 | 150 | 125 | 200 | 150 | 150 |
| Average particle size (μm) | 1.5 | 3.0 | 1.5 | 5.0 | 2.0 | 2.0 |
| WDG-WP | | | | | | |
| Triflumizole | 100 | 300 | | | 200 | |
| Thiophanate methyl | | | 600 | 600 | | 600 |
| Sodium alkylnaphthalenesulfonate | 10 | 10 | 10 | 10 | 20 | 10 |
| Sodium alkylbenzenesulfonate | 10 | 10 | | | 10 | |
| Sodium ligninsulfonate | 80 | 80 | 25 | 25 | 80 | 25 |
| Formaldehyde condensate of Sodium naphthalenesulfonate | 140 | 140 | 50 | 25 | 140 | 50 |
| Diatomaceous earth | 300 | 200 | | | 300 | |
| Calcium carbonate | | | 100 | 100 | | 100 |
| Potassium chloride | 237.5 | 137.5 | 42.5 | 17.5 | 127.5 | 92.5 |
| Average particle size (μm) | 7.0 | 6.0 | 7.0 | 7.0 | 8.0 | 7.0 |

POE: Polyoxyethylene, POP: Polyoxypropylene

The formulation examples for the water dispersible granule according to the present invention, which can be prepared in the same manner as the examples described above, are shown in Table 2.

The water to be contained in the WDG-SC is required to make the pulverized mixture into fine particles under wet milling in slurry state and the amount might be selected in a range of from 100 to 300 g. The particle size of the active ingredient in the WDG-SC may be adjusted depending on the objective for the use. The amount of water to be added after the mixing of the WDG-WP and the WDG-SC into the mixture is required to be appropriate for making the kneaded product in argillaceous state.

TABLE 2

| Example | 7 | 8 | 9 | 10 | 11 | 12 |
|---|---|---|---|---|---|---|
| WDG-SC | | | | | | |
| Clethoxim methyl | 100 | | | | | |
| Mepanipyrim | | 100 | 200 | | | |
| Thiuram | | | | 100 | | |
| Hexythiazox | | | | | 100 | 150 |
| POE tristyrylphenyl ether | 10 | 10 | 10 | | | 10 |
| Sodium polycarboxylate | 10 | 10 | 10 | 20 | | |
| POE-POP block copolymer | | | | 50 | | 20 |
| Formaldehyde condensate of Sodium phenolsulfonate | | | | 70 | | 50 |
| Sodium alkylnaphthalenesulfonate | | | | | 20 | |
| WDG-WP | | | | | | |
| Triflumizole | 300 | | | | | |
| Thiophanate methyl | | | 600 | 500 | | |

TABLE 2-continued

| Example | 7 | 8 | 9 | 10 | 11 | 12 |
|---|---|---|---|---|---|---|
| Acetamiprid | | | | | 300 | 400 |
| Fluazinam | | | 200 | | | |
| Sodium alkynaphthalenesulfonate | 20 | 10 | 10 | 20 | 20 | 10 |
| Sodium ligninsulfonate | 100 | 25 | 25 | 80 | 80 | 100 |
| Formaldehyde condensate of Sodium naphthalenesulfonate | 200 | 50 | 50 | 150 | 80 | 100 |
| Calcium carbonate | 200 | 100 | 100 | | | |
| Diatomaceous earth | | | | 200 | | |
| Clay | | | | | 200 | 100 |
| Ammonium sulfate | | | | 130 | | |
| Potassium chloride | 60 | 95 | 95 | | 180 | 60 |

Industrial Use:

Now, the advantageous effect of the present invention is explained in the following with referring the comparative examples and the comparative test examples with the examples described above.

Comparative Example 1

Same Composition as Example 1, but the Active Ingredient is Pulverized into Fine Particles Under Wet Milling Together with Other Components The compound A in an amount of 100 g, triflumizole in an amount of 100 g, tristyrylphenyl ether added with polyoxyethylene of which HLB being 15 more or less in an amount of 10 g, sodium polycarboxylate in an amount of 10 g and silicon series anti-foaming agent in an amount of 2.5 g were mixed and then added with distilled water in an amount of 300 g, and the resulting mixture was pulverized into fine particles under wet milling according to the same procedure as described in the Example 1 to prepare the WDG-SC containing the active ingredient of which average particle size being 1.5 μm.

Then, sodium alkylnaphthalenesulfonate in an amount of 10 g, sodium alkylbenzenesulfonate in an amount of 10 g, formaldehyde condensate of sodium alkylnaphthalenesulfonate in an amount of 140 g, sodium ligninsulfonate in an amount of 80 g, diatomaceous earth in an amount of 300 g and potassium chloride in an amount of 237.5 g were mixed and then pulverized into fine particles under dry milling according to the same procedure as described in the Example 1 to prepare a powder formulation of which particles having the average particle size of 7 μm.

To the obtained powder formulation in an amount of 777.5 g, the WDG-SC obtained above in an amount of 522.5 g and distilled water in an amount of 30 g were added to obtain the WDG (WDG-comparison 1) of the Comparative Example 1 according to the same procedure as described in the Example 1.

Test Example 1

The two types of WDG each in an amount of 1 g, the WDG (WDG-1) prepared in the Example 1 and the WDG (WDG-comparison 1) prepared in the Comparative Example 1, were separately added into 100 ml tap water and were dispersed while shaking. 1 ml of the obtained dispersion was placed into a petri dish with a diameter of 9 cm and dried at an ambient temperature. Then, the dispersion was exposed to sunlight (approximately 100,000 lux) and the remaining amount of the compound A on the petri dish was determined at a fixed interval by means of HPLC analysis. The remaining ratio of the compound A based on the amount of triflumizole before exposing to sunlight is shown in Table 3.

TABLE 3

| Sunlight Irradiation Time (hr) | WDG-1 | WDG-comparison 1 |
|---|---|---|
| 0 | 100% | 100% |
| 3 | 96% | 67% |
| 6 | 89% | 44% |

From the Table 3, it is demonstrated that the water dispersible granule formulation prepared according to the Example 1 is stable against sunlight and can show excellent residual activity in comparison with the WDG prepared in the Comparative Example 1.

Comparative Example 2

Example of the WDG Containing the Same Active Ingredient as One in the Example 2 Prepared by Dry Milling The compound A in an amount of 100 g, triflumizole in an amount of 300 g, sodium alkylnaphthalenesulfonate in an amount of 20 g, formaldehyde condensate of sodium alkylnaphthalenesulfonate in an amount of 140 g, sodium ligninsulfonate in an amount of 100 g, calcium carbonate in an amount of 200 g and potassium chloride in an amount of 140 g were mixed and then pulverized under dry milling according to the same procedure as described in the Example 1. However, the part of the compound A was not pulverized well and the particles having the particle size being larger than several hundreds μm remained in the pulverized powder, and therefore, it was not successful to prepare the water dispersible granule according to this process.

Comparative Example 3

Example of the WDG Containing the Same Active Ingredient as One in the Example 3 Prepared by Dry Pulverization The compound A in an amount of 150 g, thiophanate methyl in an amount of 600 g, sodium alkylnaphthalenesulfonate in an amount of 10 g, formaldehyde condensate of sodium alkylnaphthalenesulfonate in an amount of 50 g, sodium ligninsulfonate in an amount of 25 g, calcium carbonate in an amount of 100 g and potassium chloride in an amount of 65 g were mixed and then pulverized under dry milling according to the same procedure as described in the Example 1. However, the part of the compound A was not pulverized well and the particles having the particle size being larger than several hundreds μm remained in the pulverized powder, and therefore, it was not successful to prepare the water dispersible granule according to this process.

Comparative Example 4

Example of WDG Containing the Same Active Ingredient as One in the Example 4 Prepared by Wet Grinding Triflumizole in an amount of 100 g, thiophanate methyl in an amount of 600 g, block copolymer of polyoxyethylene of which HLB being 14 more or less and polyoxypropylene in an amount of 50 g, formaldehyde condensate of sodium phenolsulfonate in an amount of 70 g, tristyrylphenyl ether added with polyoxyethylene of which HLB being 15 more or less in an amount of 10 g and silicon series anti-foaming agent in an amount of 2.5 g were mixed and then added with distilled water to be required for preparing the WDG-SC, then the total amount of the mixture came to 700 g. The mixture was then pulverized under wet milling to prepare the WDG-SC containing the active ingredient having the average particle size of 5 μm.

Then, the WDG-SC was mixed with calcium carbonate in an amount of 100 g and potassium chloride in an amount of 67.5 g, and the mixture was pulverized under dry milling to prepare a powder formulation of which particles having the average particle size of 5 μm.

To the obtained powder formulation, the WDG-SC obtained above in an amount of 1,532.5 g was added, however, the resulting mixture was not prepared into argillaceous state during the kneading process due to the presence of excessive water since the water amount in the WDG-SC exceeded the required water amount for the preparation of the WDG which accordingly make unable to prepare the moist noodle-shaped product for granulation, and therefore, it was not successful to prepare the water dispersible granule according to this process.

Comparative Example 5

WDG Containing Triflumizole of which Particle Size being 2 μm

Triflumizole in an amount of 100 g, trisyrylphenyl ether added with polyoxyethylene of which HLB being 15 more or less in an amount of 10 g, sodium polycarboxylate in an amount of 10 g and silicon series anti-foaming agent in an amount of 2.5 g were mixed and then added with distilled water in an amount of 150 g, and the resulting mixture was pulverized under wet milling according to the same procedure as described in the Example 1 to prepare the WDG-SC containing the active ingredient having the average particle size of 2 μm.

Then, sodium alkylnaphthalenesulfonate in an amount of 20 g, sodium alkylbenzenesulfonate in an amount of 10 g, formaldehyde condensate of sodium alkylnaphthalenesulfonate in an amount of 140 g, sodium ligninsulfonate in an amount of 80 g, diatomaceous earth in an amount of 300 g and potassium chloride in an amount of 327.5 g were mixed and then pulverized under dry milling according to the same procedure as described in the Example 1 to prepare the powder formulation of which particles having the average particle size of 8 μm. The obtained powder formulation was then added with the WDG-SC obtained above in an amount of 272.5 g and distilled water in an amount of 200 g to prepare the WDG (WDG-comparison 5) of the Comparative Example 5 according to the same procedure as described in the Example 1.

Comparative Example 6

WDG Containing Triflumizole with the Average Particle Size of 8 μm

Triflumizole in an amount of 300 g, sodium alkylnaphthalenesulfonate in an amount of 20 g, sodium alkylbenzenesulfonate in an amount of 10 g, formaldehyde condensate of sodium alkylnaphthalenesulfonate in an amount of 140 g, sodium ligninsulfonate in an amount of 80 g, diatomaceous earth in an amount of 300 g and potassium chloride in an amount of 150 g were mixed, and the mixture was pulverized under dry milling to prepare the WG-WP of which particles containing triflumizole having the average particle size of 8 μm. The obtained WG-WP in an amount of 1,000 g was added with distilled water in an amount of 240 g to prepare the WDG (WDG-comparison 6) of the Comparative Example 6 according to the same procedure as described in the Example 1.

Test Example 2

Each of WDG containing triflumizole prepared in the Example 5 (WDG-5) and the Comparative Examples 5 and 6 (WDG-comparison 5 and WDG-comparison 6) was separately diluted at a predetermined concentration and was sprayed to apple fruits. After naturally drying the sprayed apple fruits, the spore suspension of apple scab fungus (spore concentration, $1 \times 10^5$/ml) was sprayed onto the apples on 0 and 3 days after spraying of the WDG. On 11 days later, the appearance of the infection by apple scab fungus was accessed, and the disease control efficacy in the plots sprayed with the WDG was evaluated in comparison with the plot without spraying of the WDG according to the equation presented below. The results are shown in Table 4. The preventive effect (initial activity) may be known from the effectiveness when the inoculation of the spore suspension was made just after the spraying of the WDG (0 day) and the residual effect may be known from the effectiveness when the inoculation of the spore suspension was made on 3 days after the spraying of the WDG.

Disease Control Efficacy=(1□(Area covered by scab fungus infection on the WDG-sprayed apples/ Area covered by scab fungus infection on apples without spray of the WDG))×100

TABLE 4

| Formulation | Concentration of Active Ingredient Sprayed (ppm) | Disease Control Efficacy (%) | |
|---|---|---|---|
| | | Preventive effect (Initial activity) | Residual effect |
| WDG-5 | 50 | 100 | 100 |
| | 12 | 100 | 20 |
| | 3 | 95 | 0 |
| WDG-comparison 5 | 50 | 100 | 75 |
| | 12 | 100 | 0 |
| | 3 | 90 | 0 |
| WDG-comparison 6 | 50 | 100 | 100 |
| | 12 | 100 | 12 |
| | 3 | 50 | 0 |

As shown in the Table 4, the water dispersible granule formulation (WDG-5) prepared in the Example 5 showed excellent residual effectiveness in comparison with the corresponding formulation (WDG-comparison 5) prepared in the Comparative Example 5 and excellent initial effectiveness in comparison with the formulation (WDG-comparison 6) prepared in the Comparative Example 6.

Comparative Example 7

WDG Containing Thiophanate Methyl with the Average Particle Size of 2 μm

Thiophanate methyl in an amount of 100 g, tristyrylphenyl ether added with polyoxyethylene of which HLB being 15 more or less in an amount of 10 g, sodium polycarboxylate in an amount of 10 g and silicon series anti-foaming agent in an amount of 2.5 g were mixed and the mixture was then added with distilled water in an amount of 150 g, and the resulting mixture was pulverized under wet milling according to the same procedure as described in the Example 1 to prepare the WDG-SC containing the active ingredient with the average particle size of 2 μm.

Then, sodium alkylnaphthalenesulfonate in an amount of 10 g, formaldehyde condensate of sodium alkylnaphthalenesulfonic acid in an amount of 100 g, sodium ligninsulfonate in an amount of 25 g, calcium carbonate in an amount of 100 g and potassium chloride in an amount of 115 g were mixed, and the resulting mixture was pulverized under dry milling according to the same procedure as described in the Example 1 to prepare the powder formulation of which particles having the average particle size of 7 μm. The obtained powder formulation in an amount of 877.5 g was added with the above-obtained WDG-SC in an amount of 272.5 g and distilled water in an amount of 180 g to obtain the WDG of the Comparative Example 7 (WDG-comparison 7) according to the same procedure as described in the Example 1.

Comparative Example 8

WDG Containing Thiophanate Methyl with the Average Particle Size of 7 μm

Thiophanate methyl in an amount of 700 g, sodium alkyl-naphthalenesulfonate in an amount of 10 g, formaldehyde condensate of alkylnaphthalenesulfonic acid in an amount of 50 g, sodium ligninsulfonate in an amount of 25 g, calcium carbonate in an amount of 100 g and potassium chloride in an amount of 115 g were mixed, and the resulting mixture was pulverized under dry milling to prepare the WDG-WP of which particles having the average particle size of 7 μm. The obtained WDG-WP in an amount of 1,000 g was added with distilled water in an amount of 300 g to prepare the WDG of the Comparative Example 8 (WDG-comparison 8) according to the same procedure as described in the Example 1.

Test Example 3

Each of WDG containing thiophanate methyl prepared in the Example 6 (WDG-6) and the Comparative Examples 7 and 8 (WDG-comparison 7 and WDG-comparison 8) was separately diluted at a predetermined concentration and the dilution was sprayed to sugarbeet plants (variety; Monohomare). After naturally drying the sprayed sugarbeet plants, the spore suspension of Cercospora leaf spot fungus (spore concentration, $1 \times 10^5$/ml) was sprayed onto the sugarbeet plants on 0 and 7 days after spraying of the WDG. On 11th day after the spraying, the appearance of the infection by Cercospora leaf spot fungus was accessed, and the disease control efficacy in the plots sprayed with the WDG was evaluated in comparison with the plot without spraying of the WDG according to the equation presented in the Test Example 1. The results are shown in Table 5. The preventive effect (initial activity) may be known from the effectiveness when the inoculation of the spore suspension was made just after the spraying of the WDG (0 day) and the residual effect may be known from the effectiveness when the inoculation of the spore suspension was made on 7 days after the spraying of the WDG.

TABLE 5

| Formulation | Concentration of Active Ingredient Sprayed (ppm) | Disease Control Efficacy (%) | |
|---|---|---|---|
| | | Preventive Effect (Initial Activity) | Residual Effect |
| WDG-6 | 200 | 100 | 100 |
| | 50 | 100 | 85 |
| | 12 | 100 | 0 |
| | 3 | 80 | 0 |
| WDG-comparison 7 | 200 | 100 | 95 |
| | 50 | 100 | 20 |
| | 12 | 100 | 0 |
| | 3 | 82 | 0 |
| WDG-comparison 8 | 200 | 100 | 100 |
| | 50 | 100 | 82 |
| | 12 | 75 | 0 |
| | 3 | 19 | 0 |

In the Table 5, the water dispersible granule formulation (WDG-6) prepared in the Example 6 showed excellent residual effectiveness in comparison with the corresponding formulation (WDG-comparison 7) prepared in the Comparative Example 7 and excellent initial effectiveness in comparison with the formulation (WDG-comparison 8) prepared in the Comparative Example 8.

As explained above, the present invention is directed to a process for producing a water dispersible granule formulation for agricultural chemical use, particularly comprising an active ingredient easily decomposed owing to environmental conditions, which is suitable for preparing a water dispersible granule formulation, wherein the active ingredient is required to be pulverized into fine particles in order to enhance the initial biological activity and is also required to be pulverized into coarse particles in order to enhance the residual activity. According to the present invention, the part of the active ingredients may be pulverized into fine particles under wet milling, and the other part of the active ingredients may be pulverized into coarse particles under dry milling, then kneading the both active ingredients to prepare the granules containing the both active ingredients, thereby allowing to simply and efficiently produce a water dispersible granule containing different types of particles having different particle sizes, respectively.

What is claimed is:

1. A process for providing both of high initial activity and high residual activity to a water dispersible granule formulation comprising a process for producing the water dispersible granule formulation comprising the steps of:
    wet milling a combined mixture of a first active ingredient, a wetting and dispersing agent, and water,
    pulverizing a combined mixture of a second active ingredient, a mineral carrier, and a wetting and dispersing agent under dry milling,
    admixing the mixture obtained in the wet milling step and the mixture obtained in the dry milling step, and then
    drying the admixed mixture to form a homogeneous granule formulation, wherein:
    the first active ingredient is pulverized to an average particle size value from about 0.5 µm to about 5 µm in the step of wet milling the combined mixture,
    the second active ingredient is pulverized to an average particle size value from about 3 µm to about 30 µm in the step of pulverizing the combined mixture under dry milling,
    the first active ingredient is a compound which is a solid at an ambient temperature and has a solubility in water of 1,000 ppm or less,
    the first and second active ingredients are different active ingredients,
    the second active ingredient is an agricultural chemical selected from the group consisting of an insecticide, a fungicide, and a herbicide,
    each of the first and second active ingredients have two different average particle sizes, and
    the second active ingredient has coarser particles than the first active ingredient.

2. The process according to claim 1, wherein the first active ingredient is selected from a group consisting of triflumizole, thiuram, fluazinam, anilazine, captan, hexythiazox, benzoximate, tebufenpyrad, ziram, thiophanate methyl, mepanipyrim, clethoxim methyl, triazine, N'-cyclopropylmethyloxy-N-phenylacetyl-2,3-difluoro-6-trifluoromethylbenzamidine, and combinations thereof.

3. The process according to claim 1, wherein the second active ingredient is selected from a group consisting of triflumizole, thiuram, fluazinam, anilazine, captan, hexythiazox, benzoximate, tebufenpyrad, ziram, thiophanate methyl, mepanipyrim, clethoxim methyl, triazine, N'-cyclopropylmethyloxy-N-phenylacetyl-2,3-difluoro-6-trifluoromethylbenzamidine, and combinations thereof.

4. A process for providing both of high initial activity and high residual activity to a water dispersible granule formulation comprising a process for producing the water dispersible granule formulation comprising the steps of:
    wet milling a combined mixture of a first active ingredient, a wetting and dispersing agent, and water,
    pulverizing a combined mixture of a second active ingredient, a mineral carrier, and a wetting and dispersing agent under dry milling,
    admixing the mixture obtained in the wet milling step and the mixture obtained in the dry milling step, and then
    drying the admixed mixture to form a homogeneous granule formulation, wherein:
    the first active ingredient is pulverized to an average particle size value from about 0.5 µm to about 5 µm in the step of wet milling the combined mixture,
    the second active ingredient is pulverized to an average particle size value from about 3 µm to about 30 µm in the step of pulverizing the combined mixture under dry milling,
    the first active ingredient is a compound which is a solid at an ambient temperature and has a solubility in water of 1,000 ppm or less,
    the first and second active ingredients are different active ingredients,
    the first and second active ingredients are agricultural chemicals selected from the group consisting of an insecticide, a fungicide, and a herbicide,
    each of the first and second active ingredients have two different average particle sizes, and
    the second active ingredient has coarser particles than the first active ingredient.

5. A process for providing both of high initial activity and high residual activity to a water dispersible granule formulation comprising a process for producing the water dispersible granule formulation comprising the steps of:
    wet milling a combined mixture of a first active ingredient, a wetting and dispersing agent, and water,
    pulverizing a combined mixture of a second active ingredient, a mineral carrier and a wetting and dispersing agent under dry milling,
    admixing the mixture obtained in the wet milling step and the mixture obtained in the dry milling step, and then drying the admixed mixture to form a homogeneous granule formulation, wherein:

the first active ingredient is pulverized to an average particle size value from about 0.5 μm to about 5 μm in the step of wet milling the combined mixture, the second active ingredient is pulverized to an average particle size value from about 3 μm to about 30 min in the step of pulverizing the combined mixture under dry milling, the first active ingredient is a compound which is a solid at an ambient temperature and has solubility in water of 1,000 ppm or less, the first and second active ingredients are different active ingredients, the first and second active ingredients are independently selected from a group consisting of triflumizole, thiuram, fluazinam, anilazine, captan, hexythiazox, benzoximate, tebufenpyrad, ziram, thiophanate methyl, mepanipyrim, clethoxim methyl, triazine, N'-cyclopropylmethyloxy-N-phenylacetyl-2,3-difluoro-6-trifluoromethylbenz-amidine, and combinations thereof, each of the first and second active ingredients have two different average particle sizes, and the second active ingredient has coarser particles than the first active ingredient.

* * * * *